United States Patent
Schellenbaum

[11] 3,991,124
[45] Nov. 9, 1976

[54] ALKYLPHENOLS
[75] Inventor: Max Schellenbaum, Muttenz, Switzerland
[73] Assignee: Ciba-Geigy Corporation, Ardsley, N.Y.
[22] Filed: Feb. 5, 1976
[21] Appl. No.: 655,586

Related U.S. Application Data
[63] Continuation of Ser. No. 390,629, Aug. 22, 1973, abandoned.

[30] Foreign Application Priority Data
Aug. 28, 1972 Switzerland........................ 12688/72

[52] U.S. Cl................ 260/623 R; 8/161; 8/200; 8/10.1; 106/15 AF; 106/228; 106/38.22; 117/13; 117/26; 424/70; 424/59; 424/49; 424/78; 424/80; 424/167; 424/181; 424/190; 424/193; 424/280
[51] Int. Cl.².......................... C07C 39/30
[58] Field of Search............... 260/623 R, 623 H

[56] References Cited
UNITED STATES PATENTS

| | | | |
|---|---|---|---|
| 2,318,390 | 5/1943 | Hartman et al.............. | 260/623 R |
| 2,778,857 | 1/1957 | Beman..................... | 260/623 R |
| 2,901,515 | 8/1959 | Rigterink................. | 260/623 R |
| 2,922,736 | 1/1960 | Spalding.................. | 162/161 |
| 3,449,443 | 6/1969 | Dietzler.................. | 260/623 R |

OTHER PUBLICATIONS
Blackman et al. "Arch. Biochem. & Biophys." 45–54 (1955).
Chien et al. "Chem. Abst." vol. 34, pp. 1979–1980 (1940).
Suter et al. "Chem. Abst." vol. 46, p. 3512 (1952).

*Primary Examiner*—James O. Thomas, Jr.
*Assistant Examiner*—W. B. Lone
*Attorney, Agent, or Firm*—Frederick H. Rabin

[57] ABSTRACT

"New alkylphenols of formula I

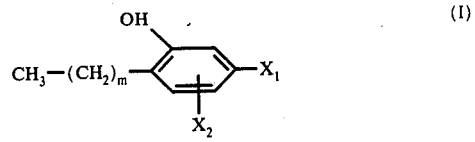

method of preparing this new compounds and their use for the control of harmful microorganisms, and helminths and for protecting organic materials."

6 Claims, No Drawings

ALKYLPHENOLS

This is a continuation of application Ser. No. 390,629 filed on Aug. 22, 1973, now abandoned.

The present invention relates to novel alkylphenols, to processes for their preparation, to agents containing these new compounds, and to the use of the new compounds for the control of microorganisms, as feed additives for animals of commercial value, and for the preservation of materials.

According to the invention, new alkylphenols of formula I

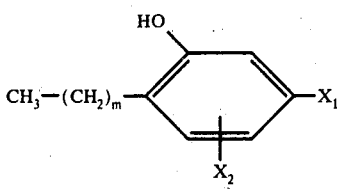

are suggested, wherein $X_1$ and $X_2$ represent halogen, and $m$ an integer from 1 to 11.

For the attainment of the aims and objectives according to the invention, the preferred compounds of formula I are those wherein $X_1$ and $X_2$ represent chlorine or bromine, and $m$ is an integer from 1 to 6, whereby $X_2$ is preferably in the meta- or para-position with respect to the OH-group.

A number of alkylphenols and their fields of application for the control of microorganisms, particularly gram-positive bacteria, are already known (cp. K. H. Wallhauser and H. Schmidt, "Sterilisation, Desinfektion, Konservierung, Chemotherapie"(Sterilisation, Disinfection, Preservation, Chemotherapy), Georg Thieme Verlag (publishers), 1967).

Surprisingly, it has now been found that, by virtue of their special substitution, the novel alkylphenols suggested according to the invention are very effective also against gram-negative bacteria and against mold fungi. The compounds advantageously have an exceptionally wide range of action, but only slight toxicity. They can also be used with success as supplementary feed agents for the promotion of growth of animals of commercial value. A particular advantage of the compounds according to the invention is that, even with relatively low concentrations, they have an action ranging from a simple inhibitory action to one resulting in the complete destruction of the microorganisms to be controlled. With regard to the application of the compounds according to the invention, the fact that these compounds are colourless and create negligible smell renders them particularly valuable.

The alkylphenols according to the invention can be prepared by the reduction of ketones for formula II

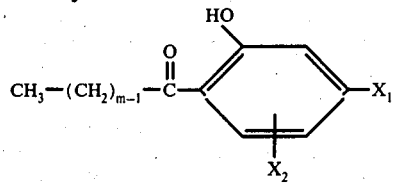

in which $x_1$, $X_2$ and m have the above given meanings.

The reduction of such ketones can be performed by various methods known per se. Thus, for example, the reduction method according to Wolff-Kishner (cp. D. Todd, Organic Reactions 4, 378; 1948) can be successfully applied. This is a process in which the ketone is firstly converted into the hydrazone, and this then decomposed with sodium ethylate, at elevated temperature and under pressure, to the corresponding hydrocarbon. In a modified process according to Huang-Minlon (cp. Huang-Minlon, Journal of the American Chemical Society 68, 2487; 1946), the decomposition of the hydrazone is effected in an inert solvent at elevated temperature, but under normal pressure, with the aid of an inorganic base. The procedure applied with advantage is one whereby firstly the ketone is heated in an inert, high-boiling, water-miscible solvent together with an excess of hydrazine hydrate and an alkali hydroxide to 100°–150° C, and then the formed hydrazone, after removal of the water and the excess hydrazine hydrate by distillation, decomposed by heating to 180°–220° C.

Especially good yields are obtained when the solvents employed are glycols, such as ethylene glycol, diethylene glycol or triethylene glycol. The alkali hydroxide used is advantageously sodium or potassium hydroxide; as a rule, 3 to 7 moles per mole of ketone to be reduced. The formation of the hydrazone is best effected where the process is performed at a temperature of 120°–140° C with an excess of 3 to 7 moles of hydrazine hydrate per mole of ketone. The decomposition of the formed hydrazone is most advantageously effected at a temperature of between 190° and 210° C. The reaction times required for the formation of hydrazone are between 30 minutes and 3 hours; the times for decomposition of the hydrazone between 1 and 5 hours.

The Clemmensen reduction (cp. E. Clemmensen, 'Berichte der deutschen Chemischen Gesellschaft' 46, 1837; 1913 and likewise 47, 51,681; 1914, as well as E. L. Martin, Journal of the American Society 58, 1438; 1936) constitutes a further good method for the preparation of the alkylphenols according to the invention from the corresponding ketones. The reduction is carried out in this case by the heating of the ketones with amalgamated zinc and hydrochloric acid, optionally in the presence of an organic solvent. Owing to the poor water-solubility of the ketones of formula II, it is advantageous if the reduction be performed in the presence of water-miscible organic solvents such as, e.g. ethanol, acetic acid or dioxane. The reduction gives particularly good yields when 8 to 15 gram atoms of zinc amalgam are used per mole of ketone to be reduced.

The reaction temperature may be varied, for example, between 20° C and the boiling temperature of the solvent employed; the reaction times are accordingly from 48 hours to 1 hour.

A further reduction method is the hydrogenolysis of the dialkylthioketals or ethylenethioketals, obtained from the ketones of formula II, with Raney nickel (cp. L. F. Fieser and W.-Y. Huang, Journal of the American Chemical Society 75, 5356; 1953).

Reference is also made to catalytic hydrogenation of the ketones of formula II to the alkylphenols according to the invention.

The ketones of formula II used as starting products are known (cp. A. B. Sen and P. M. Bhargava, Journal of the Indian Chemical Society 26, 287–290; 1949), or are prepared by methods known per se, e.g. from the corresponding alkanecarboxylic acid phenyl esters by the Fries reaction (cp. Baltzly et al., Journal of American Chemical Society 77, 2522; 1955, or G. A. Olah, Friedel-Crafts and Related Reactions 1964, page 499). The reaction can be performed in the melt or in the presence of an organic solvent, e.g. nitrobenzene. On heating of the corresponding phenyl esters together with aluminium chloride, there are then formed the ketones of formula II.

A further method of preparing the alkylphenols according to the invention is the chlorination or bromination of compounds of formula III

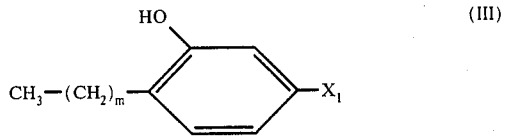

wherein $X_1$ and m have the above given meanings.

The compounds of formula III are known (cp. J. Org. Chem. 26, 3631 – 38, 1961), or can be prepared by processes known per se.

The compounds of formula I have good solubility in organic solvents. Their water-soluble salts, especially the alkali metal and alkaline-earth metal salts, are likewise effective, and are of special importance where an application in aqueous medium and soaps is concerned.

The use of the antimicrobial compounds of the present invention is possible on a very broad basis, particularly for the preservation of organic substrates against infestation by harmful and pathogenic microorganisms. The mentioned antimicrobic agents are hence suitable for use as preservatives and disinfectants for commercial products of all kinds.

Among the commercial products that can be preserved with the aid of the compounds of formula I according to the invention, mention may be made of the following:

Glues, bonding agents, coating agents, textile auxiliaries and processing agents, dyeing and printing pastes and similar preparations based on organic and inorganic dyestuffs or pigments, also such preparations containing, as admixtures, casein or other organic compounds. Also wall and ceiling coatings, e.g. those which contain an albuminous binder, are protected from infestation by pests by an addition of compounds according to the invention. Application for the preservation of wood is likewise possible.

The compounds according to the invention can be used as preservatives also in the cellulose and paper industry, one purpose of application being the prevention of the known mucus formation, caused by microorganisms, in the plant used for paper production.

The action of the compounds according to the invention can be utilised also in preserving and disinfecting finishes imparted to plastics. With the use of softeners, it is advantageous to add the antimicrobial agent dissolved or dispersed in the softener to the plastics. It is preferable that care be taken to obtain an as homogeneous a distribution in the plastics as possible. The plastics having antimicrobial properties can be employed for commodities of all kinds where it is desired to have effectiveness against a wide range of germs, such as, e.g. bacteria and fungi: thus, for example, for foot mats, bathroom curtains, seats, foot grids in swimming baths, wall coverings, etc.. Floor and furniture polishes having a disinfecting action are obtained by incorporation of the compounds according to the invention into the appropriate wax compositions.

The compounds according to the invention are used with advantage to impart to fibres and textiles a preserving and disinfecting finish: they can be applied to natural and to synthetic fibres and exercise there a permanent action against harmful (also pathogenic) microorganisms, e.g. fungi and bacteria. The addition of the compounds can be made before, at the same time as, or after a treatment of these textiles with other substances, e.g. with dyeing or printing pastes, flameproofing agents, soft-feel agents and other finishing agents, etc..

Textiles treated thus offer also protection against the occurrence of perspiration odour, such as is caused by microorganisms.

The forms in which the active substances according to the invention are applied can be in line with the usual formulations. Agents used for the finishing or for the protecting of textiles should contain the active substances in a finely divided form: in particular, solutions, dispersions and emulsions of the active substances find therefore application. Aqueous dispersions can be obtained, for example, from pastes or concentrates, and can be applied as liquids or in the aerosol form.

The aqueous solutions or dispersions advantageously contain surface-active agents; for example, anionactive compounds such as soaps and other carboxylates (e.g. alkali salts of higher fatty acids), derivatives of sulphur-oxyacids (e.g. sodium salt of dodecylbenzenesulphonic acid, water-soluble salts of sulphuric acid monoesters of higher molecular alcohols or of their polyglycol ethers, such as, for instance, soluble salts of dodecyl alcohol sulphate or of dodecyl alcohol polyglycol ether sulphate), derivatives of phosphorus-oxyacids (e.g. phosphates), derivatives with acid (electrophilic) nitrogen in the hydrophilic group (e.g. disulphine salts), cation-active surface-active agents, such as amines and their salts (e.g. lauryldiethylenetriamine), onium compounds, amine oxides or nonionic surface-active agents, such as polyhydroxy compounds, surface-active agents based on mono- or polysaccharide, higher-molecular acetylene glycols, polyglycol ethers (e.g. polyglycol ethers of higher fatty alcohols, polyglycol ethers of higher molecular-alkylated phenols). In addition, the liquor can contain conventional auxiliaries, such as water-soluble perborates, polyphosphates, carbonates, silicates, optical brighteners, softeners, acid reacting salts such as ammonium- or zincsilicofluoride, or certain organic acids such as oxalic acid, also finishing agents, e.g. those based on synthetic resin or on starch.

The textile materials can be impregnated with the active substances, e.g., by means of hot or cold aqueous dyeing, bleaching, chroming or aftertreatment baths, whereby various textile-finishing processes are suitable, such as, e.g. the padding or exhaust process.

On account of their better solubility in organic solvents, the active substances are also suitable for application from non-aqueous media: the materials to be finished or preserved can in this case be simply impregnated with the solutions.

Applicable organic solvents are, for example, trichloroethylene, methylene chloride, hydrocarbons, propylene glycol, methoxyethanol, ethoxyethanol or dimethylformamide, to which may also be added distributing agents (e.g. emulsifiers, such as sulphated castor oil, fatty alcohol sulphates, etc.), and/or other auxiliaries.

Depending on the purpose of application, the content of active substances according to the present invention can be between 0.1 and 50 g, preferably between 1 and 30 g, of active substance per litre of treatment liquid.

The active substances according to the present invention can be used on their own, or together with other known antimicrobial textile-preserving agents.

Suitable as textiles to be finished or preserved are both fibres of natural origin, such as cellulose-containing fibres, e.g. cotton, or polypeptide-containing fibres, e.g. wool or silk, and fibre materials of synthetic origin, such as those based on polyamide, polyacrylonitrile or polyester, as well as mixtures of these fibres.

In most cases, the textile materials are adequately preserved against infestation by fungi and bacteria by a content of 0.01 to 5%, preferably 0.1 to 3%, of active substance, relative to the weight of the textile materials.

By combination of the compounds according to the invention with interfacial-active substances, especially with washing-active substances, detergents and cleansing agents having excellent antibacterial or antimycotic action are obtained.

The detergents and cleansing agents can be in any desired form, e.g. in liquid, pasty, solid, flake or granular form. The compounds according to the invention can be incorporated into anion-active compounds, such as soaps and other carboxylates (e.g. alkali salts of higher fatty acids), derivatives of sulphur-oxyacids (e.g. sodium salt of dodecylbenzenesulphonic acid, water-soluble salts of sulphuric acid monoesters of higher-molecular alcohols or of their polyglycol ethers, such as, for instance, soluble salts of dodecyl alcohol sulphate or of dodecyl alcohol polyglycol ether sulphate), derivatives of phosphorus-oxyacids (e.g. phosphates), derivatives with acid (electrophilic) nitrogen in the hydrophilic group (e.g. disulphine salts), as well as into cation-active surfaceactive agents, such as amines and their salts (e.g. lauryldiethylenetriamine), onium compounds, amine oxides or nonionic surface-active agents, such as polyhydroxy compounds, surface-active agents based on mono- or polysaccharide, higher-molecular acetylene glycols, polyglycol ethers (e.g. polyglycol ethers of higher fatty alcohols, polyglycol ethers of higher-molecular alkylated phenols), or into mixtures of different surfactants. The antimicrobial activity of the new compounds is retained, with this application, to the full extent. The active-substance content of the detergents and cleansing agents, relative to the weight of this agent, is generally from 0.01 to 5%, mostly 0.1 to 3%. Aqueous preparations of such detergents and cleansing agents containing compounds according to the invention can be employed, for example, for the antimicrobial finishing of textile materials, since the active substance is able to be absorbed substantively on to the textile material. They are likewise suitable as antimicrobial cleansing agents in the food and drink industry, e.g. in breweries, dairies, cheese factories and slaughter houses.

Furthermore, the compounds according to the invention can also be used in cosmetic preparations, such as, e.g. volatile oils, bath salts, brilliantines, ointments, face water, hair-dyeing preparations, hair oils, hair dressings, skin creams, skin oils, Eau-de-Cologne, perfumes, powders, rouge, depilatories, sun-ray filter creams, tooth-cleansing products, etc., in consequence of which there is additionally imparted to these products an antimicrobial action. In general, an activesubstance content, relative to the total weight of the product, of 0.01 to 5%, preferably of 0.1 to 3%, suffices.

For the purpose of disinfection and preservation, the compounds of formula I can also be used in combination with known antimicrobial agents. These include, e.g.:

Halogens and halogen compounds with active halogen e.g. sodium hypochlorite, calcium hypochlorite, chloride of lime, sodium-p-toluenesulphochloramide, p-toluenesulphodichloramide, N-chlorosuccinimide, 1,3-dichloro-5,5-dimethyl-hydantoin, trichloroisocyanuric acid, potassiumdichloroisocyanurate, iodine, iodine trichloride, complex compounds of iodine and iodine trichloride with surfaceactive agents such as polyvinylpyrrolidone, alkylphenoxypolyglycols, polyoxypropylene glycols, alkylaminoethanesulphonic acids and -sulfphonates, alkylarylsulphonates, quaternary ammonium compounds.

Boron compounds e.g. boric acid, borax.

Organometallic compounds e.g. bis-tributyltin oxide, triphenyltin hydroxide, tributyltin salicylate, tributyltin chloride, phenylmercury borate, phenylmercury acetate.

Alcohols e.g. hexyl alcohol, trichloroisobutyl alcohol, 1,2-propylene glycol, triethylene glycol, benzyl alcohol, 4-chlorobenzyl alcohol, 2,4- and 3,4-dichlorobenzyl alcohol, 2-phenylethyl alcohol, 2-(4-chlorophenyl) ethyl alcohol, ethylene glycol monophenyl ether, menthol, linalool and 2-bromo-2-nitro-propanediol-1,3.

Aldehydes e.g. formaldehyde, paraformaldehyde, glutaraldehyde, benzaldehyde, 4-chlorobenzaldehyde, 2,4- and 3,4-dichlorobenzaldehyde, cinnamaldehyde, salicylic aldehyde, 3,5-dibromosalicylic aldehyde, 4-hydroxybenzaldehyde, anisaldehyde and vanillin.

Carboxylic acids and derivatives e.g. trichloroacetic acid, monobromoacetic acid glycol ester, Na- and Ca-propionate, caprylic acid, undecylenic acid, Zn-undecylenate, sorbic acid, K- and Ca-sorbate, lactic acid, malonic acid, acenitic acid, citric acid, benzoic acid, 4-chlorobenzoic acid, benzoic acid benzyl ester, salicylic acid, 4-chlorosalicylic acid-n-butylamide, salicylanilide, 3,4', 5-tribromosalicylanilide, 3,3',4',5-tetrachlorosalicylanilide, 4-hydroxybenzoic acid, 4-hydroxybenzoic acid ethyl ester, gallic acid, mandelic acid, phenylpropiolic acid, phenoxyacetic acid, dehydracetic acid and vanillic acid propyl ester.

Phenols e.g. phenol, mono- and polychlorophenols, cresols, 4-chloro-3-methylphenol, 4-chloro-3,5-dimethylphenol, thymol, 4-chlorothymol, 4-t-amylphenol, saligenin, 4-n-hexylresorcin, carvacrol, 2-phenylphenol, 2-benzyl-4-chlorophenol, 2,2'-dihydroxy-5,5'-dichlorodiphenylmethane, 2,2'-dihydroxy-3,3', 5,5',6,6'-hexachloro-diphenylmethane, 2,2'-dihydroxy-5,5'-dichloro-diphenylsulphide, 2,2'-dihydroxy-3,3',5,5'-tetrachlorodiphenylsulphide, 2-hydroxy-2',4,4'-trichlorodiphenyl ether and dibromosalicyl.

Quinones e.g. 2,5-dimethylquinone, 2,3,5,6-tetrachloro-benzoquinone, 1,4-2,3-dichloro-1,4-naphthoquinone.

Carbonic acid derivatives e.g. pyrocarbonic acid diethyl ester, tetramethylthiuram disulphide, 3,4,4'-trichloro-N,N'diphenylurea, 3-trifluoromethyl-4,4'-dichloro-N,N'-diphenylurea, N-3-trifluoromethylphenyl-N'-2-ethylhexyl-urea, 1,6-bis-(4'-chlorophenyl-di-guanidino)-hexane, dodecyl-methylguanidine acetate, ammonium rhodanide, 4,4'-diamidino$\alpha,\omega$-diphenoxy-hexane.

Amines e.g. dodecylpropylenediamine, dodecyldiethylenetriamine and diaminobenzene-dihydroiodide.

Quaternary ammonium compounds e.g. alkyl-dimethyl-benzyl-ammonium chloride, alkyl-dimethyl-ethyl-benzyl-ammonium chloride, dodecyl-dimethyl3,4-dichlorobenzyl-ammonium chloride, dodecyl-di-(2-hydroxyethyl)-benzyl-ammonium chloride, dodecyl-di-(2-hydroxyethyl)-benzyl-ammonium-pentachlorophenolate, dodecyl-di-(2-hydroxyethyl)-benzyl-ammonium-4-methyl benzoate, dodecyl-dimethyl-phenoxyethyl-ammonium bromide, 4-diisobutyl-phenoxyethoxyethyl-dimethyl-benzyl-ammonium chloride, 4-diisobutyl-cresoxyethoxyethyl-dimethyl-benzylammonium chloride, dimethyl-didecyl-ammonium chloride, cetyltrimethylammonium bromide, dodecyl-pyridinium chloride, cetyl-pyridinium chloride, dodecyl-isoquinolinium chloride, decamethylene-bis-4-aminoquinaldinium dichloride, $\alpha$-(p-tolyl)-dodecyl-trimethyl-ammonium methosulphate, (dodecanoyl-N-methyl-aminoethyl)-(phenylcarbamoylmethyl)-dimethylammonium chloride.

Quaternary phosphonium compounds e.g. dodecyl-triphenyl-phosphonium bromide.

Amphoteric compounds e.g. dodecyl-di-(aminoethyl)-glycine.

Heterocyclic compounds e.g. 2-mercaptopyridine-N-oxide, Na- and Zn-salt of 2-mercaptopyridine-N-oxide, 2,2'-dithiopyridine-1,1'-di-N-oxide, 8-hydroxyquinoline, 5-chloro-8-hydroxyquinoline, 5-chloro-7-iodine-8-hydroxyquinoline, 5,7-dichloro-8-hydroxyquinoline, 5,7-dichloro-8-hydroxyquinaldine, bis-2-methyl-4-amino-quinolyl-carbamide-hydrochloride, 2-mercaptobenzthiazole, 2-(2'-hydroxy-3',5'-dichlorophenyl)-5-chlorobenzimidazole, 2-aminoacridine-hydrochloride, 5,6-dichlorobenzoxazolone, 1-dodecyl-2-iminoimidazolinehydrochloride and 6-chloro-benzisothiazolone.

The applicability of compounds of formula I for the control of microorganisms, particularly of bacteria and fungi, and for the preserving of organic materials and objects against infestation by microorganisms is very extensive. Thus, for example, they can be incorporated direct into the material to be preserved, e.g. into material having a synthetic resin base, such as polyamides and polyvinyl chloride, into paper-treatment liquors, into printing thickeners made from starch or cellulose derivatives, into lacquers and paints which contain, for example, casein, into cellulose, viscous spinninng solutions, paper, into animal mucus or oils, into permanent coatings based on polyvinyl alcohol, cosmetic articles, and into ointments or powders. They can also be added to preparations of inorganic or organic pigments for the painting industry, to softeners, etc.

The compounds of formula I can be used moreover in the form of their organic solutions, e.g. as so-called sprays, or as dry-cleaning agents, or for the impregnation of wood, suitable organic solvents being preferably solvents immiscible with water, particularly petroleum fractions, but also solvents miscible with water, such as lower alcohols, e.g. methanol or ethanol or ethylene glycol monomethyl ether, or -monoethyl ether. A number of the new compounds can be used also in aqueous solution.

Furthermore, they can be used together with wetting or dispersing agents, in the form of their aqueous dispersions, e.g. for the preservation of substances which tend to rot, such as for the preservation of leather, paper, etc.

Solutions or dispersions of active substances, which can be employed for the perservation of these materials, preferably have an active-substance content of at least 0.005 g/liter, e.g. 0.01 to 5, preferably 0.1 to 3 g/liter.

The compounds of the present invention also have an excellent growth-promoting action in the case of animals of commercial value, e.g. pigs and poultry, as well as ruminants, such as cattle or sheep.

The active substances can be administered to the animals perorally or via the abomasum, or by means of injection, in the form of solutions, emulsions, suspensions, powders, tablets, boluses and capsules, either as a single dose or as repeated doses. The active substances or mixtures containing them may also be added to the feed or to the drinking trough, or can be contained in so-called feed pre-mixings.

By virtue of their wide microbicidal range of action, the compounds of the present invention can also be used in veterinary medicine for the control of pathogenic microorganisms on and in the animal, particularly on the skin and in the intestinal tract and urogenital system. For the control of pathogenic microoganisms in veterinary medicine and/or for the attainment of a growth-promoting action in the case of animals of commercial value, the compounds of the present invention can be combined with the following substances.

1. Antibiotics

Penicillin and its derivatives,
Cephalosporin and its derivatives,
Chloramphenicol,
Tetracyclines (e.g. chlorotetracycline, oxytetracycline),
Rifamycin and its derivatives (e.g. Rifampin)
Lincomycin
Bacitracin and its salts,
Pyrrolnitrin
Myxin,
Streptomycin
Nigericin
Parvulin
Spiramycin
Neomycin
Thiopeptin
Tylosin.

2. Sulphonamides

N'-(3,4-dimethyl-5-isoxazolyl)-sulphanilamide,
N'-2-pyrazinylsulphanilamide,
2,4-dimethoxy-6-sulphamylamido-1,3-diazine,
N'-(4-methyl-2-pyrimidyl)-sulphanilamide.

3. Nitrofurans 3-(5-nitrofurfurylideneamino)-2-oxazolidinone, 5-morpholinomethyl-3-(5-nitrofurfurylideneamino)-2-oxazolidinone,
3-amino-6-[2-(nitro-2-furyl)vinyl]-pyridazine,
1,5-di-(5'-nitro-2'-furyl)-penta-1,4-dien-one-(3)-2'-amidinohydrazone-hydrochloride.

4. Diaminopyrimidines
2,4-diamino-5-(3,4,5-trimethoxybenzyl)-pyrimidine,
2,4-diamino-5-(3,4-dimethoxybenzyl)-pyrimidine,
2,4-diamino-5-(p-chlorophenyl)-6-ethylpyrimidine.

5. Hydroxyquinolines
5,7-dichloro-8-hydroxyquinaldine,
5-chloro-7-iodo-8-hydroxyquinoline.

6. Hydroxyquinolinecarboxylic acids and hydroxynaphthyridine acids
1-ethyl-1,4-dihydro-7-methyl-4-oxo-1,8-naphthyridine-3-carboxylic acid,
oxolinic acid.

7. Quinoxaline-di-N-oxides
quinoxaline-1,4-di-N-oxide,
3-(1,4-dioxo-2-quinoxalinemethylene)-carbazinic acid methyl ester.

8. Halogenated hydroxydiphenyl ethers:
2-hydroxy-2'4,4'-trichloro-dipheyl ether.

9. Nitrohydroxydiphenyl ethers.

10. Optionally halogenated salicylic acid anilides.

11. Triarylmethylimidazoles:
di-(phenyl)-2-chlorophenyl-imidazolyl(1)-methane.

12. Vitamins.

13. 3-Hydroxy-2-methyl-4-pyrone.

14. 2-Mercaptoimidazole.

15. Ethoxylated alcohols such as $R-O(CH_2CH_2O)_nH$.

16. 2-Bromo-5-nitrothiazole.

17. Guanidines.

18. N-Substituted aminoacetic acids.

19. β-Nitropropionic acid.

20. Phenylcyclopropylamine.

21. 2-(4-Thiazolyl)-benzimidazole.

22. Piperazine and its salts.

23. Benzodiazepinone derivatives.

24. Dihydroxydiphenylsulphides.

25. 4,5Dihydroxy-2,4,6-octatrienedicarboxylic acids.

26. 2-Formyl-4chlorophenoxyacetic acids.

27. Straight-chain aliphatic alcohols.

28. 2-Chloro-10-(3-dimethylaminopropyl)-phenothiazine.

29. Acetoxybenzoic acid.

30. Auxins:
3,5-di-sec.butyl-α,β,δ-trihydroxy-1-cyclopentenevaleric acid,
3,5-di-sec.butyl-δ-hydroxy-β-oxo-1-cyclopentenevaleric acid.

Besides having a good microbicidal action, the compounds of the present invention have a good authelmintic action. In therapeutically effective doses, they are excellently compatible, and are outstandingly effective against:

Helminths nematodes, such as ascaridae, trichostrongylidae ancylostomatidae or strongylidae;
cestodes, such as anoplocephalidae or taenidae.

The agents containing the active substances of formula I according to the invention can be used for the control of parasitic helminths in the case of domestic animals and animals of commercial value such as cattle, sheep, goats, horses, pigs, cats, dogs and poultry. They can be administered to the animals both as a single dose or as repeated doses, the single doses being, depending on the species of animal, preferably between 25 and 1000 mg of active substance per kg of body weight. A better action is obtained in some cases by a protracted administration, or smaller overall doses may suffice. The active substances or mixtures containing them can also be added to the feed or to the drinking trough. The prepared feed contains the substances of formula I preferably in a concentration of ca. 0.05 to 1 percent by weight.

EXAMPLE 1

An amount of 163.0 g of 3,5-dichlorophenol is dissolved in 200 ml of benzene and 79.1 g of anhydrous pyridine; there is then added dropwise at 5°–15° C with stirring, in the course of 1 hour, a solution of 134.6 g of caproic acid chloride in 200 ml of benzene. The temperature of the reaction mixture is allowed to rise to 20° C; the precipitated pyridine hydrochloride is filtered off, the benzene solution washed with water and, after drying over sodium sulphate, completely concentrated in a water-jet vacuum. The caproic acid-3,5-dichlorophenyl ester remaining (255 g) is heated to 60° C, and an addition then made to it at this temperature in the course of 10 minutes, with stirring, of 400 g of anhydrous aluminium chloride. After 5 hours, the liquid reaction mixture is poured, as stirring is maintained, into 3 liters of ice water. The initially oily precipitate fully crystallises during subsequent stirring. It is filtered off, washed with water and dried in vacuo to obtain 210.7 g of 2-hydroxy-4,6-dichlorocaprophenone, M.P. 39°–41° C.

A mixture of 52.2 g of 2-hydroxy-4,6-dichlorocaprophenone, 60 g of hydrazine hydrate, 67 g of potassium hydroxide and 300 ml of diethylene glycol is refluxed for 3 hours. The excess hydrazine hydrate is distilled off, and the reaction solution subsequently heated for 2 hours at 195°–200° C. It is then stirred into 2 liters of ice water, the whole acidified with concentrated hydrochloric acid and extracted with chloroform. The chloroform solution is dried over sodium sulphate, and concentrated by evaporation. From the oil remaining, the compound of the formula

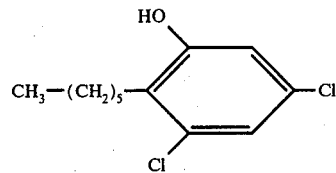

is isolated by chromatography on silica gel, with the use of benzene as the eluant. For further purification, the compound is recrystallised from hexane. The yield is 38.2 g; M.P. 48°–49° C. Instead of by chromatography, the compound can be isolated also by vacuum distillation; B.P. 89° C/0.005 mmHg.

EXAMPLE 2

A solution of 32 g of bromine in 20 ml of carbon tetrachloride is added dropwise at −10° to −15° C in the course of 1 hour, with stirring, to a solution of 34.1 g of 5-chloro-2-propyl-phenol in 150 ml of carbon tetrachloride. After stirring to room temperature, the reaction solution is completely concentrated by evaporation and the resulting compound of the formula

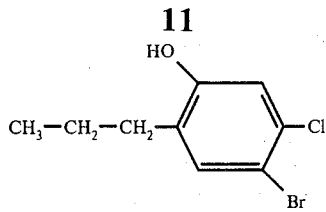

purified by vacuum distillation. The yield is 34.0 g; B.P. 90° – 91° C / 0.06 mm Hg.

The compounds in the following Table A according to formula III can be prepared by the procedure of the proceeding examples, or by one of the previously described methods:

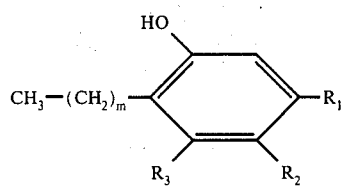

Table A

| Compound No. | $R_1$ | $R_2$ | $R_3$ | m | Melting point ° C |
|---|---|---|---|---|---|
| 1 | Cl | H | Cl | 5 | 48 – 49 |
| 2 | Cl | H | Cl | 1 | 59 – 60 |
| 3 | Cl | H | Cl | 2 | oil (boiling point) 86 – 87° C/0,005 mmHg) |
| 4 | Cl | H | Cl | 3 | 60 – 61 |
| 5 | Cl | H | Cl | 4 | 43 – 44 |
| 6 | Cl | H | Cl | 6 | oil (boiling point) 114 – 117° C/0.05 mmHg) |
| 7 | Cl | H | Cl | 7 | oil (boiling point 130 – 133° C/0,005 mmHg) |
| 8 | Cl | Cl | H | 1 | 80 – 81 |
| 9 | Cl | Cl | H | 3 | oil (boiling point) 102 – 104° C/0,0005 mmHg) |
| 10 | Cl | Cl | H | 4 | 43 – 44 |
| 11 | Cl | Cl | H | 5 | 39 – 40 |
| 12 | Cl | Cl | H | 6 | oil (B.P.: 150° C/0.005 mmHg) |
| 13 | Cl | Cl | H | 2 | oil (B.P.: 78 – 82° C/0,005mmHg) |
| 14 | Cl | Br | H | 4 | 59 – 60 |
| 15 | Cl | Br | H | 3 | 44 – 46 |
| 16 | Cl | Br | H | 1 | 90 – 91 |
| 17 | Cl | Br | H | 2 | oil (B.P.: 90 – 91/0,06 mmHg) |
| 18 | Br | Cl | H | 1 | 83 – 84 |
| 19 | Br | Cl | H | 2 | 56 – 57 |
| 20 | Br | Cl | H | 3 | 46 – 47 |
| 21 | Br | Br | H | 3 | 40 – 41 |
| 22 | Br | Br | H | 4 | 60 – 61 |
| 23 | Br | H | Br | 3 | 83 – 84 |
| 24 | Br | Br | H | 1 | 91 – 92 |
| 25 | Br | Br | H | 2 | 60 – 61 |

Determination of the minimum inhibiting concentrations (MIC) against bacteria and fungi Stock solutions (1.5%) of the compounds of formula I in methylcellosolve are prepared, and these subsequently diluted so that the incorporation of 0.3 ml of the stock solution in each case and of each dilution in 15 ml each time of warm nutrient-agar produces a concentration series of 300, 100, 30, 10, 3, 1, and so forth, ppm of active substance in the agar. The mixtures whilst still arm are poured into dishes and, after solidification, inoculated with the following test organisms:

Gram-positive bacteria

*Staphylococcus aureus,*
*Sarcina ureae,*
*Streptoococcus faeclis,*
*Streptococcus agalactiae,*
*Corynebacterium diphtheroides,*
*Bacillus subtilis,*
*Mycobacterium phlei.*

Gram-negative bacteria

*Escherichia coli,*
*Salmonella pullorum,*
*Salmonella chlorerae-suis,*
*Bordetella bronchiseptica,*
*Pasteurella multocida,*
*Proteus vulgaris.*
*Proteus rettgeri,*
*Pseudomonas fluorescens,*
*Pseudomonas aeroginosa.*

Fungi

*Trichophyton gypseum,*
*Trichophyton gallinae,*
*Trichophyton verrucosum,*
*Candida albicans,*
*Candida krusci,*
*Aspergillus niger,*
*Aspergillus flavus,*
*Penicillium funiculosum,*
*Penicillium expansum,*
*Trichoderma viride,*
*Fusarium oxysporum,*
*Chaetonium globosum,*
*Alternaria tenuis,*
*Paccilomyces varioti,*
*Stachybotrys atra.*

After an incubation of 48 hours at 37° C (bacteria) and 5 days at 28° C (fungi), the minimum concentration (ppm) of the active substances with which the growth of the test organisms is inhibited is determined.

The record values for the minimum inhibiting concentration (MIC) in the case of compounds of formula I are clearly below the starting concentration of 300 ppm.

Determination of the microbicidal action

A. In order to determine whether the active substances had destroyed the test germs (biocidal effect) or had merely inhibited them in their growth (biostatic effect), sterile filter paper disks of 20 mm diameter are placed on the inoculation sites of the germs exhibiting no growth, and, after a contact time of 30 minutes, the germs transferred by means of these disks to sterile agar blocked with respect to the active substances with Tween 80. The contact time is again 30 minutes. If no growth of the transferred germs on the secondary agardish is observed, the germs will have been destroyed by the active substance in the first dish, i.e. the active substance in the concentrations concerned has a biocidal action on the germs examined.

The following additional test is carried out for confirmation of the preceding finding:

B. Active substances of formula I are used to prepare the following solutions:

5% of active substance,
5% of Na-N-cocos-$\beta$-aminopropionate,
20% of permutite water,
70% of ethylcellosolve (ethylene glycol monoethyl ether).

Aliquot parts of these solutions are converted with sterile distilled water into emulsions of 1000 ppm, 500 ppm, 250 ppm and 125 ppm active-substance content.

Samples of 9.9 ml of the emulsions are inoculated with 0.1 ml of germ suspensions (ca. $10^7$ germs/ml).

Test organisms:

*Staphylococcus aureus,*
*Strephylococcus faccalis*
*Bacillus subtilis,*
*Proteus vulgaris.*

After an action time of 1 minute, a loop of the inoculated emulsions is placed in each case into 10 ml of sterile brain-heart-infusion-broth; after an incubation time of 24 hours at 37°, the brain-heart-infusion-broth is examined for cloudiness (germ growth).

The examined compounds of formula I exhibited in the above tests a biocidal action.

What we claim is:

1. alkylphenols of formula I

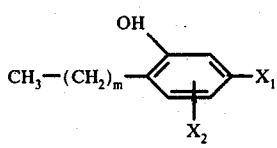

wherein
  $X_1$ and $X_2$ represent halogen, and $m$ is an integer from 1 to 11.

2. Alkyphenols according to claim 1 wherein
  $X_1$ and $X_2$ represent chlorine or bromine, and
  $m$ is an integer from 1 to 6.

3. Alkylphenols according to claim 2 wherein the radical
  $X_2$ is in the meta- or para-position with respect to the OH-group.

4. Alkylphenols according to claim 3 which correspond to the formula

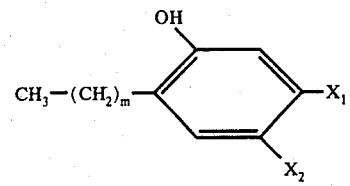

wherein $X_1$ and $X_2$ represent chlorine or bromine and $m$ is an integer from 1 to 6.

5. Alkylphenol according to claim 1, corresponding to the formula

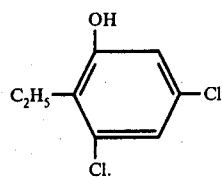

6. Alkylphenol according to claim 4, corresponding to the formula

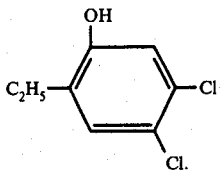

* * * * *